United States Patent
Heidenhain et al.

(10) Patent No.: US 10,290,810 B2
(45) Date of Patent: May 14, 2019

(54) POLYMER AND ORGANIC ELECTRONIC DEVICE

(71) Applicants: Cambridge Display Technology Limited, Godmanchester (GB); Sumitomo Chemical Company Limited, Tokyo (JP)

(72) Inventors: Sophie Barbara Heidenhain, Lower Cambourne (GB); Richard Owoare, Legon (GH); Gary Watts, Cambridgeshire (GB); Jonathan Pillow, Godmanchester (GB)

(73) Assignees: Cambridge Display Technology Limited, Godmanchester (GB); Sumitomo Chemical Company Limited, Tokyo (JP)

( * ) Notice: Subject to any disclaimer, the term of this patent is extended or adjusted under 35 U.S.C. 154(b) by 492 days.

(21) Appl. No.: 14/909,045

(22) PCT Filed: Jul. 29, 2014

(86) PCT No.: PCT/GB2014/052315
§ 371 (c)(1),
(2) Date: Jan. 29, 2016

(87) PCT Pub. No.: WO2015/015183
PCT Pub. Date: Feb. 5, 2015

(65) Prior Publication Data
US 2016/0190458 A1    Jun. 30, 2016

(30) Foreign Application Priority Data

Jul. 31, 2013 (GB) .................................. 1313699.9

(51) Int. Cl.
*H01L 51/00* (2006.01)
*C09K 11/06* (2006.01)
(Continued)

(52) U.S. Cl.
CPC .......... *H01L 51/0039* (2013.01); *C07C 25/22* (2013.01); *C08G 61/12* (2013.01);
(Continued)

(58) Field of Classification Search
CPC . H01L 51/0039; H01L 51/0043; H01L 51/56; H01L 51/5012; C08G 61/12;
(Continued)

(56) References Cited

U.S. PATENT DOCUMENTS

2007/0205714 A1    9/2007   Busing et al.
2009/0203866 A1*   8/2009   Schafer ................. C07C 17/263
                                                           526/256
(Continued)

FOREIGN PATENT DOCUMENTS

EP    1 571 170 A1    9/2005
JP    2004-111228 A   4/2004
(Continued)

OTHER PUBLICATIONS

Combined Search and Examination Report dated Jan. 28, 2014 for Application No. GB 1313699.9.
(Continued)

*Primary Examiner* — Ruiyun Zhang
(74) *Attorney, Agent, or Firm* — Wolf, Greenfield & Sacks, P.C.

(57) ABSTRACT

A polymer comprising a repeat unit of formula (I): wherein $R^1$ in each occurrence is independently H or a substituent, and the two groups $R^1$ may be linked to form a ring; $R^2$ in each occurrence is independently a substituent; $Ar^1$ in each occurrence is independently an aryl or heteroaryl group that may be unsubstituted or substituted with one or more substituents; $R^3$ in each occurrence is independently a substituent; each n independently is 0, 1, 2 or 3 with the proviso
(Continued)

that at least one n=1; and each m is independently 0 or 1. The polymer may be a light-emitting 103 of an organic light-emitting device.

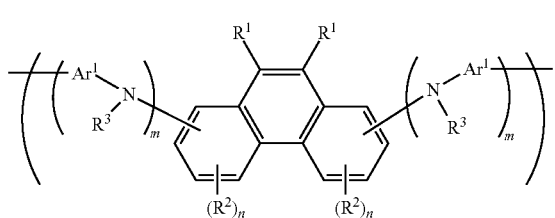

(I)

20 Claims, 3 Drawing Sheets

(51) Int. Cl.
*C08L 65/00* (2006.01)
*H05B 33/10* (2006.01)
*C08G 61/12* (2006.01)
*C07C 25/22* (2006.01)
*C09K 11/02* (2006.01)
*H01L 51/56* (2006.01)
*H01L 51/50* (2006.01)

(52) U.S. Cl.
CPC .......... *C08G 61/122* (2013.01); *C08L 65/00* (2013.01); *C09K 11/025* (2013.01); *C09K 11/06* (2013.01); *H01L 51/0005* (2013.01); *H01L 51/0043* (2013.01); *H01L 51/56* (2013.01); *H05B 33/10* (2013.01); *C08G 2261/12* (2013.01); *C08G 2261/148* (2013.01); *C08G 2261/149* (2013.01); *C08G 2261/1412* (2013.01); *C08G 2261/18* (2013.01); *C08G 2261/314* (2013.01); *C08G 2261/3142* (2013.01); *C08G 2261/3245* (2013.01); *C08G 2261/344* (2013.01); *C08G 2261/411* (2013.01); *C08G 2261/512* (2013.01); *C08G 2261/95* (2013.01); *C09K 2211/1416* (2013.01); *C09K 2211/1425* (2013.01); *C09K 2211/1433* (2013.01); *H01L 51/5012* (2013.01)

(58) Field of Classification Search
CPC .......... C08G 61/122; C08G 2261/12; C08G 2261/18; C08G 2261/314; C08G 2261/3142; C08G 2261/344; C08G 2261/95; C08G 2261/148; C08G 2261/149; C07C 25/22; C09K 11/025; C09K 11/06; C09K 2211/1416; C09K 2211/1433

USPC ............ 428/690, 917; 313/504; 252/301.16, 252/301.35, 500; 257/40
See application file for complete search history.

(56) References Cited

U.S. PATENT DOCUMENTS

2009/0207346 A1 8/2009 Ohuchi et al.
2012/0097938 A1 4/2012 Meyer et al.

FOREIGN PATENT DOCUMENTS

WO WO 2005/104264 A1 11/2005
WO WO 2008/006743 A1 1/2008
WO WO 2010/136112 A1 12/2010
WO WO 2014/102543 A2 7/2014

OTHER PUBLICATIONS

International Search Report and Written Opinion dated Sep. 4, 2014 for Application No. PCT/GB2014/052315.
International Preliminary Report on Patentability dated Feb. 11, 2016 for Application No. PCT/GB2014/052315.
Suh et al., Stabilized Blue Emission from Organic Light-Emitting Diodes Using Poly(2,6-(4,4-bis(2-ethylhexyl)-4H-cyclopenta [def]phenanthrene)). Macromolecules. Jul. 1, 2005;38(15):6285-9.
Shimizu et al., Palladium-catalyzed double cross-coupling reaction of 1,2-bis(pinacolatoboryl) alkenes and -arenes with 2,2'-dibromobiaryls: annulative approach to functionalized polycyclic aromatic hydrocarbons. Tetrahedron. Aug. 6, 2011;67(41):8014-26.
Vanormelingen et al., Conformational Steering in Substituted Poly(3,6-phenanthrene)s: A Linear and Nonlinear Optical Study. Macromolecules. Jun. 23, 2009;42(12):4282-7.
Boden et al., New diformyldihydroxyaromatic precursors for luminescent Schiff base macrocycles: Synthesis, characterization, and condensation studies. Can. J. Chem. 2008;86(1):50-64.
Boden et al., Social and Antisocial[3+3]Schiff Base Macrocycles with Isomeric Backbones. J. Org. Chem. 2008;73:8069-72.
Lin et al., Palladium-Catalyzed Annulation of 2,2'-Diiodobiphenyls with Alkynes: Synthesis and Application of Phenathrenes. J. Org. Chem. 2012;77:9979-88.
Mallory et al., Phenacenes: A Family of Graphite Ribbons. 2. Synthesis of Some [7] Phenacenes and an [11] Phenacene by Stibene-like Photocyclizations. J. Am. Chem. Soc. 1997;119; 2119-24.
Mallory et al., Phenacenes: a family of graphite ribbons. Part 3: Iterative strategies for the synthesis of large phenacenes. Tetrahedron. 2001;57; 3715-24.
Meier et al., Band-Shaped Structures by Repetitive Cycloaddition Reactions of Benzo[1,2-b:4-5-b']bisthiete. Liebigs Ann. Recueil. 1997:1173-7.
Nodiff et al., Antimalarial Phenanthrene Amino Alcohols. 3. Halogen-Containing 9-Phenanthrenemethanols. Journal of Medicinal Chemistry. 1975;18(10):1011-19.

* cited by examiner

POLYMER AND ORGANIC ELECTRONIC DEVICE

RELATED APPLICATIONS

The present application is a national stage filing under 35 U.S.C. § 371 of international PCT application, PCT/GB2014/052315, filed Jul. 29, 2014, which claims priority to United Kingdom patent application, GB 1313699.9, filed Jul. 31, 2013, each of which is incorporated herein by reference in its entirety.

BACKGROUND OF THE INVENTION

Electronic devices containing active organic materials are attracting increasing attention for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material combine to form an exciton that releases its energy as light.

A light emitting layer may comprise a semiconducting host material and a light-emitting dopant wherein energy is transferred from the host material to the light-emitting dopant. For example, J. Appl. Phys. 65, 3610, 1989 discloses a host material doped with a fluorescent light-emitting dopant (that is, a light-emitting material in which light is emitted via decay of a singlet exciton).

Phosphorescent dopants are also known (that is, a light-emitting dopant in which light is emitted via decay of a triplet exciton).

A hole-transporting layer may be provided between the anode and light-emitting layer of an OLED.

Light-emitting materials include small molecule, polymeric and dendrimeric materials. Suitable light-emitting polymers include poly(arylene vinylenes) such as poly(p-phenylene vinylenes) and polymers containing arylene repeat units, such as fluorene repeat units.

A layer of an OLED, e. g. the light-emitting layer, may be formed by depositing a formulation containing the materials of the layer and a solvent followed by evaporation of the solvent, which requires use of soluble organic polymer materials allowing solution processing in device manufacture.

US2007/205714 discloses polymers comprising at least 5 mol % of repeat units of the following formula:

$$---[Y-[X]_n]_m \text{—(phenanthrene)—} [[X]_n-Y]_m---$$

wherein X is $-CR^1=CR^1-$, $C\equiv C$ or $N-Ar$ and Y is a divalent aromatic or heteroaromatic ring system having 2 to 40 C atoms.

SUMMARY OF THE INVENTION

In a first aspect the invention provides a polymer comprising a repeat unit of formula (I):

(I)

[Chemical structure of formula (I)]

wherein:
$R^1$ in each occurrence is independently H or a substituent;
$R^2$ in each occurrence is independently a substituent;
$Ar^1$ in each occurrence is independently an aryl or heteroaryl group that may be unsubstituted or substituted with one or more substituents;
$R^3$ in each occurrence is independently a substituent;
each n independently is 0, 1, 2 or 3 with the proviso that at least one n=1; and
each m is independently 0 or 1.

In a second aspect the invention provides a monomer of formula (Im):

(Im)

[Chemical structure of formula (Im)]

wherein $R^1$, $R^2$, $R^3$, Ar, n and m are as described in the first aspect and LG is a leaving group.

In a third aspect the invention provides a method of forming a polymer according to the first aspect, the method comprising the step of polymerising a monomer according to the second aspect.

In a fourth aspect the invention provides a formulation comprising a polymer according to the first aspect and one or more solvents.

In a fifth aspect the invention provides an organic electronic device comprising a layer comprising a polymer according to the first aspect.

Optionally according to the fifth aspect the organic electronic device is an organic light-emitting device comprising an anode, a cathode and at least one organic semiconducting layer including an organic light-emitting layer between the anode and the cathode, wherein the at least one organic semiconducting layer comprises a polymer according to the first aspect.

In a sixth aspect the invention provides a method of forming an organic light-emitting device according to the fifth aspect, the method comprising the steps of:

(i) depositing the formulation according to the fourth aspect over one of the anode and cathode;
(ii) evaporating the at least one solvent to form the organic semiconducting layer comprising a polymer according to the first aspect; and
(iii) forming the other of the anode and cathode over the organic semiconducting layer.

DESCRIPTION OF THE DRAWINGS

The invention will now be described in more detail with reference to the drawings in which.

DETAILED DESCRIPTION OF THE INVENTION

Figure 1:
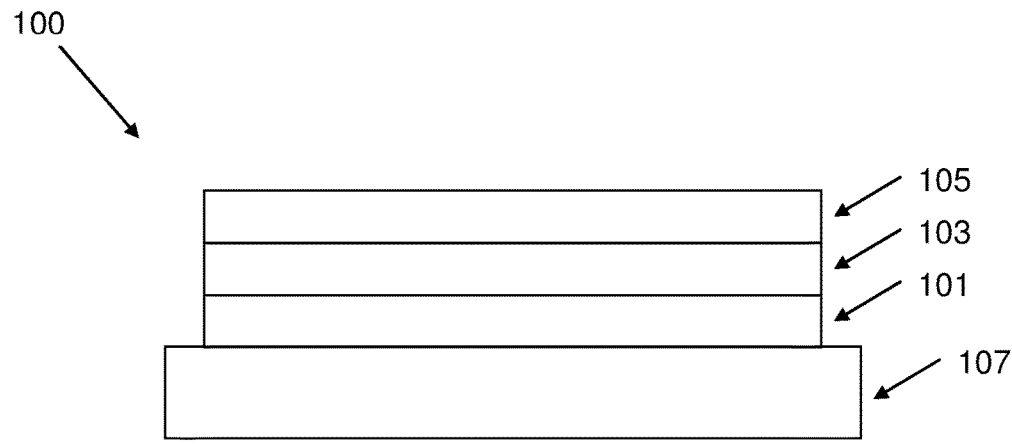
FIG. 1 illustrates schematically an OLED according to an embodiment of the invention.

FIG. 1 illustrates an OLED 100 according to an embodiment of the invention comprising an anode 101, a cathode 105 and a light-emitting layer 103 between the anode and cathode. The device 100 is supported on a substrate 107, for example a glass or plastic substrate.

One or more further layers may be provided between the anode 101 and cathode 105, for example hole-transporting layers, electron transporting layers, hole blocking layers and electron blocking layers. The device may contain more than one light-emitting layer.

Preferred device structures include:
Anode/Hole-injection layer/Light-emitting layer/Cathode
Anode/Hole transporting layer/Light-emitting layer/Cathode
Anode/Hole-injection layer/Hole-transporting layer/Light-emitting layer/Cathode
Anode/Hole-injection layer/Hole-transporting layer/Light-emitting layer/Electron-transporting layer/Cathode.

At least one of a hole-transporting layer and hole injection layer may be present. Optionally, both a hole injection layer and hole-transporting layer are present.

A polymer comprising a repeat unit of formula (I) is provided in a layer of the device. The polymer may be provided in one or more of light-emitting layer 103; a hole-transporting layer; an electron-transporting layer; and a charge-blocking layer.

A layer containing a polymer comprising a repeat unit of formula (I) may consist essentially of the polymer, or the polymer may be mixed with one or more further materials.

If the polymer is present in light-emitting layer 103 then the polymer may emit light itself when in operation, or it may function as a host material used in combination with one or more fluorescent or phosphorescent materials of the light-emitting layer.

The repeat unit of formula (I) may have formula (II):

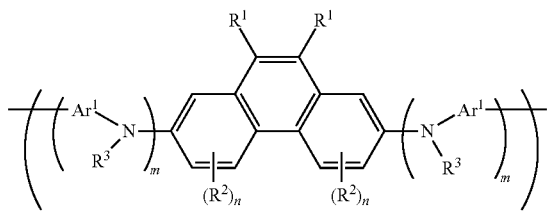

(II)

wherein $R^1$, $R^2$, $R^3$, $Ar^1$, n and m are as described above.

Linking the repeat unit of formula (I) through its 2- and 7-positions, as in the repeat unit of formula (II), may increase conjugation across the repeat unit as compared to repeat units of formula (I) linked through other positions.

The repeat unit of formula (I) may have formula (III):

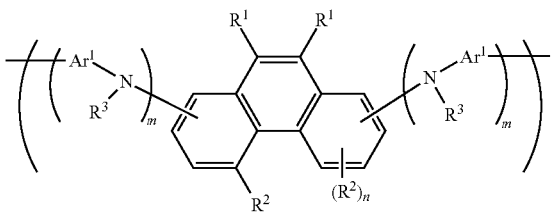

(III)

wherein $R^1$, $R^2$, $R^3$, $Ar^1$ and m are as described above, and n is 0, 1, 2 or 3.

Optionally, the polymer has formula (IVa) or (IVb):

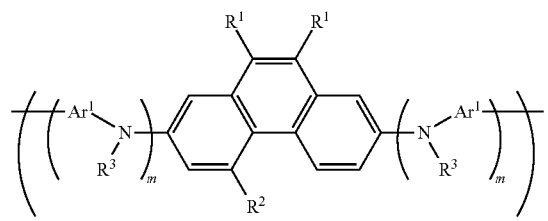

(IVa)

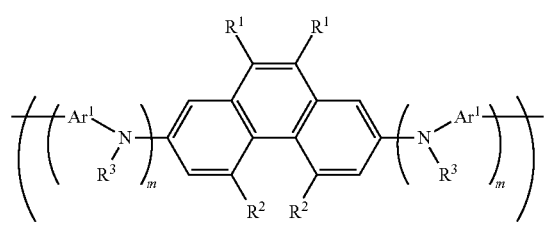

(IVb)

By providing substituent(s) $R^2$ remote from the linking positions of the repeat unit of formula (I), the substituents may alter the properties of the polymer, such as its viscosity in solution at a given concentration, without creating steric hindrance with the N atom(s) in the case where m is 1, or without creating steric hindrance with the adjacent repeat units in the case where m=0.

Each $R^1$ may independently be selected from the group consisting of:

$C_{1-30}$ alkyl wherein one or more non-adjacent C atoms may be replaced with O, S, $NR^4$, C=O and —COO— wherein $R^4$ is a substituent, and wherein one or more H atoms of the $C_{1-20}$ alkyl may be replaced with F; and aryl or heteroaryl that may be substituted or unsubstituted with one or more substituents.

$R^4$ may be a $C_{1-20}$ hydrocarbyl group, for example $C_{1-20}$ alkyl, phenyl, or phenyl substituted with one or more alkyl groups.

Each $R^1$ may be a $C_{1-40}$ hydrocarbyl group, for example a group selected from $C_{1-20}$ alkyl, unsubstituted phenyl, and phenyl substituted with one or more alkyl groups. Two groups $R^1$ may be linked to form a ring that may be unsubstituted or substituted with one or more substituents, for example substituted with one or more $C_{1-20}$ alkyl groups.

Optionally, each $R^2$ is independently selected from the group consisting of:

$C_{1-20}$ alkyl wherein one or more non-adjacent C atoms may be replaced with O, S, $NR^4$, C=O and —COO— wherein $R^4$ is as described above, and wherein one or more H atoms of the $C_{1-20}$ alkyl may be replaced with F; and aryl or heteroaryl that may be substituted or unsubstituted with one or more substituents.

Each $R^2$ may be a $C_{1-40}$ hydrocarbyl group, for example a group selected from $C_{1-20}$ alkyl, unsubstituted phenyl, and phenyl substituted with one or more alkyl groups.

Optionally, each $R^2$ is independently a $C_{1-10}$ alkyl group.

Optionally, one n is 1 and the other n is 0.

In an embodiment, each m is 0. In another embodiment, at least one m is 1. If one or both m is 1 then the amine groups of the repeat unit of formula (I) may provide hole-transporting functionality in a light-emitting layer or in a hole-transporting layer of an OLED.

If at least one m is 1 then $Ar^1$ in each occurrence may independently be a phenyl group that may be unsubstituted or substituted with one or more substituents. Optionally, substituents of $Ar^1$ may be selected from $C_{1-20}$ alkyl wherein one or more non-adjacent C atoms may be replaced with O, S, $NR^4$, C=O and —COO— wherein $R^4$ is a substituent as described above, and wherein one or more H atoms of the $C_{1-20}$ alkyl may be replaced with F If at least one m is 1 then $R^3$ in each occurrence may independently be a $C_{1-40}$ hydrocarbyl group, for example $C_{1-20}$ alkyl, phenyl, or phenyl substituted with one or more alkyl groups.

Optionally, the polymer comprises 1-50 mol %, optionally 5-40 or 10-40 mol % of the repeat unit of formula (I).

Exemplary repeat units of formula (I) include the following:

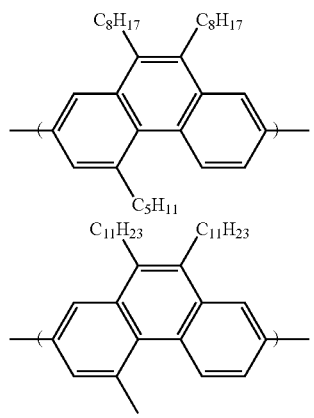

The polymer may contain only repeat units of formula (I), or it may be a copolymer containing repeat units of formula (I) and one or more further co-repeat repeat units.

Exemplary co-repeat units include arylene and heteroarylene repeat units, each of which may be unsubstituted or substituted with one or more substituents, and charge-transporting repeat units. Co-repeat units may be selected according to the intended use of the polymer.

Exemplary arylene co-repeat units include arylene repeat units, for example 1,2-, 1,3- and 1,4-phenylene repeat units, 3,6- and 2,7-linked fluorene repeat units, indenofluorene, naphthalene and anthracene repeat units, and stilbene repeat units, each of which may be unsubstituted or substituted with one or more substituents, for example one or more $C_{1-30}$ hydrocarbyl substituents.

One preferred class of arylene repeat units is phenylene repeat units, such as phenylene repeat units of formula (VI):

wherein q in each occurrence is independently 0, 1, 2, 3 or 4, optionally 1 or 2; p is 1, 2 or 3; and $R^7$ independently in each occurrence is a substituent.

Where present, each $R^7$ may independently be selected from the group consisting of:

alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F;

aryl and heteroaryl groups that may be unsubstituted or substituted with one or more substituents, preferably phenyl substituted with one or more $C_{1-20}$ alkyl groups;

a linear or branched chain of aryl or heteroaryl groups, each of which groups may independently be substituted, for example a group of formula —$(Ar^3)_r$ wherein each $Ar^3$ is independently an aryl or heteroaryl group and r is at least 2, preferably a branched or linear chain of phenyl groups each of which may be unsubstituted or substituted with one or more $C_{1-20}$ alkyl groups; and a crosslinkable-group, for example a group comprising a double bond such and a vinyl or acrylate group, or a benzocyclobutane group.

In the case where $R^7$ comprises an aryl or heteroaryl group, or a linear or branched chain of aryl or heteroaryl groups, the or each aryl or heteroaryl group may be substituted with one or more substituents $R^8$ selected from the group consisting of:

alkyl, for example $C_{1-20}$ alkyl, wherein one or more non-adjacent C atoms may be replaced with O, S, substituted N, C=O and —COO— and one or more H atoms of the alkyl group may be replaced with F;

$NR^9{}_2$, $OR^9$, $SR^9$, $SiR^9{}_3$ and fluorine, nitro and cyano;

wherein each $R^9$ is independently selected from the group consisting of alkyl, preferably $C_{1-20}$ alkyl; and aryl or heteroaryl, preferably phenyl, optionally substituted with one or more $C_{1-20}$ alkyl groups.

Substituted N, where present, may be —$NR^9$— wherein $R^9$ is as described above.

Preferably, each R⁷, where present, is independently selected from $C_{1-40}$ hydrocarbyl, and is more preferably selected from $C_{1-20}$ alkyl; unsubstituted phenyl; phenyl substituted with one or more $C_{1-20}$ alkyl groups; a linear or branched chain of phenyl groups, wherein each phenyl may be unsubstituted or substituted with one or more substituents; and a crosslinkable group.

If p is 1 then exemplary repeat units of formula (VI) include the following:

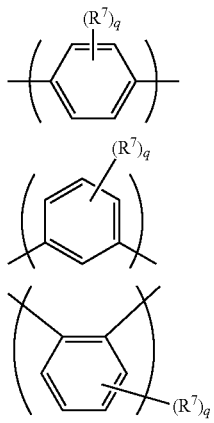

A particularly preferred repeat unit of formula (VI) has formula (VIa):

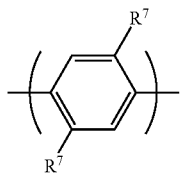

(VIa)

Substituents R⁷ of formula (VIa) are adjacent to linking positions of the repeat unit, which may cause steric hindrance between the repeat unit of formula (VIa) and adjacent repeat units, resulting in the repeat unit of formula (VIa) twisting out of plane relative to one or both adjacent repeat units.

Exemplary repeat units where p is 2 or 3 include the following:

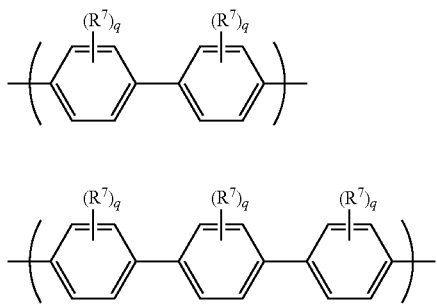

A preferred repeat unit has formula (VIb):

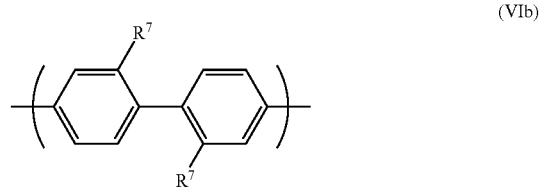

(VIb)

The two R⁷ groups of formula (VIb) may cause steric hindrance between the phenyl rings they are bound to, resulting in twisting of the two phenyl rings relative to one another.

In one optional embodiment, the repeat unit of formula (I) may be the only polycyclic aromatic repeat unit of the polymer. In another optional embodiment, the polymer may contain one or more polycyclic aromatic repeat units in addition to the repeat unit of formula (I).

An exemplary further polycyclic aromatic repeat unit is optionally substituted fluorene, such as repeat units of formula (VII):

(VII)

wherein R⁷ in each occurrence is the same or different and is a substituent as described with reference to formula (VI), and wherein the two groups R⁷ may be linked to form a ring; R¹⁰ is a substituent; and d is 0, 1, 2 or 3.

Different substituents R⁷ may be as described in WO 2012/104579, the contents of which are incorporated herein by reference.

The aromatic carbon atoms of the fluorene repeat unit may be unsubstituted, or may be substituted with one or more substituents R¹⁰. Exemplary substituents R¹⁰ are alkyl, for example $C_{1-20}$ alkyl, wherein one or more non-adjacent C atoms may be replaced with O, S, NH or substituted N, C=O and —COO—, optionally substituted aryl, optionally substituted heteroaryl, alkoxy, alkylthio, fluorine, cyano and arylalkyl. Particularly preferred substituents include $C_{1-20}$ alkyl and substituted or unsubstituted aryl, for example phenyl. Optional substituents for the aryl include one or more $C_{1-20}$ alkyl groups.

Substituted N, where present, may be —NR¹¹— wherein R¹¹ is $C_{1-20}$ alkyl; unsubstituted phenyl; or phenyl substituted with one or more $C_{1-20}$ alkyl groups.

The extent of conjugation of repeat units of formula (VII) to aryl or heteroaryl groups of adjacent repeat units may be controlled by (a) linking the repeat unit through the 3- and/or 6-positions to limit the extent of conjugation across the repeat unit, and/or (b) substituting the repeat unit with one or more substituents R¹⁰ in or more positions adjacent to the linking positions in order to create a twist with the adjacent repeat unit or units, for example a 2,7-linked fluorene carrying a $C_{1-20}$ alkyl substituent in one or both of the 3- and 6-positions.

The repeat unit of formula (VII) may be an optionally substituted 2,7-linked repeat unit of formula (VIIa):

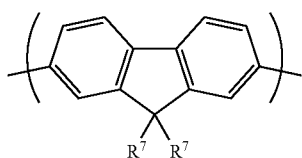

(VIIa)

Optionally, the repeat unit of formula (VIIa) is not substituted in a position adjacent to the 2- or 7-position. Linkage through the 2- and 7-positions and absence of substituents adjacent to these linking positions provides a repeat unit that is capable of providing a relatively high degree of conjugation across the repeat unit.

The repeat unit of formula (VII) may be an optionally substituted 3,6-linked repeat unit of formula (VIIb)

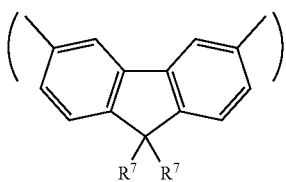

(VIIb)

The extent of conjugation across a repeat unit of formula (VIIb) may be relatively low as compared to a repeat unit of formula (VIIa).

Another exemplary further polycyclic aromatic ring system has formula (VIII) wherein $R^7$, $R^{10}$ and d are each independently as described with reference to Formula (VII), and wherein two groups $R^7$ may be linked to form an unsubstituted or substituted ring, for example a ring substituted with one or more $C_{1-20}$ alkyl groups:

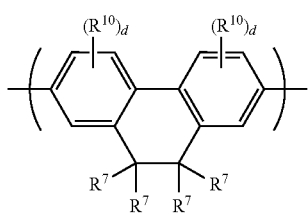

(VIII)

Further arylene co-repeat units include: naphthalene repeat units; anthracene repeat units; pyrene repeat units; and perylene repeat units. Each of these arylene repeat units may be linked to adjacent repeat units through any two of the aromatic carbon atoms of these units. Specific exemplary linkages include 9,10-anthracene; 2,6-anthracene; 1,4-naphthalene; 2,6-naphthalene; and 2,5-perylene. Each of these repeat units may be substituted or unsubstituted, for example substituted with one or more $C_{1-40}$ hydrocarbyl groups.

The polymer may contain one or more hole transporting repeat units. Exemplary hole transporting repeat units may be repeat units of materials having a electron affinity of 2.9 eV or lower and an ionisation potential of 5.8 eV or lower, preferably 5.7 eV or lower.

Preferred hole-transporting repeat units are (hetero) arylamine repeat units, including repeat units of formula (IX):

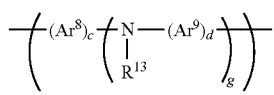

(IX)

wherein $Ar^8$ and $Ar^9$ in each occurrence are independently selected from substituted or unsubstituted aryl or heteroaryl with the proviso that $Ar^8$ and $Ar^9$ are not phenanthrene, g is greater than or equal to 1, preferably 1 or 2, $R^{13}$ is H or a substituent, preferably a substituent, and c and d are each independently 1, 2 or 3.

$R^{13}$, which may be the same or different in each occurrence when g>1, is preferably selected from the group consisting of alkyl, for example $C_{1-20}$ alkyl, $Ar^{10}$, a branched or linear chain of $Ar^{10}$ groups, or a crosslinkable unit that is bound directly to the N atom of formula (IX) or spaced apart therefrom by a spacer group, wherein $Ar^{10}$ in each occurrence is independently optionally substituted aryl or heteroaryl. Exemplary spacer groups are $C_{1-20}$ alkyl, phenyl and phenyl-$C_{1-20}$ alkyl.

Any of $Ar^8$, $Ar^9$ and, if present, $Ar^{10}$ in the repeat unit of Formula (IX) may be linked by a direct bond or a divalent linking atom or group to another of $Ar^8$, $Ar^9$ and $Ar^{10}$. Preferred divalent linking atoms and groups include O, S; substituted N; and substituted C.

Any of $Ar^8$, $Ar^9$ and, if present, $Ar^{10}$ may be substituted with one or more substituents. Exemplary substituents are substituents $R^{10}$, wherein each $R^{10}$ may independently be selected from the group consisting of:

substituted or unsubstituted alkyl, optionally $C_{1-20}$ alkyl, wherein one or more non-adjacent C atoms may be replaced with optionally substituted aryl or heteroaryl, O, S, substituted N, C=O or —COO— and one or more H atoms may be replaced with F; and a crosslinkable group attached directly to the fluorene unit or spaced apart therefrom by a spacer group, for example a group comprising a double bond such and a vinyl or acrylate group, or a benzocyclobutane group Preferred repeat units of formula (IX) have formulae 1-3:

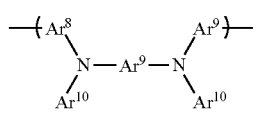

1

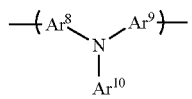

2

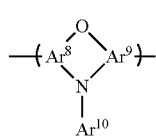

3

In one preferred arrangement, $R^{13}$ is $Ar^{10}$ and each of $Ar^8$, $Ar^9$ and $Ar^{10}$ are independently and optionally substituted with one or more $C_{1-20}$ alkyl groups. $Ar^8$, $Ar^9$ and $Ar^{10}$ are preferably phenyl.

In another preferred arrangement, the central $Ar^9$ group of formula (IX) linked to two N atoms is a polycyclic aromatic that may be unsubstituted or substituted with one or more substituents $R^{10}$. Exemplary polycyclic aromatic groups are naphthalene, perylene, anthracene and fluorene.

In another preferred arrangement, $Ar^8$ and $Ar^9$ are phenyl, each of which may be substituted with one or more $C_{1-20}$ alkyl groups, and $R^{13}$ is —$(Ar^{10})_r$- wherein r is at least 2 and wherein the group —$(Ar^{10})_r$- forms a linear or branched chain of aromatic or heteroaromatic groups, for example 3,5-diphenylbenzene wherein each phenyl may be substituted with one or more $C_{1-20}$ alkyl groups. In another preferred arrangement, c, d and g are each 1 and $Ar^8$ and $Ar^9$ are phenyl linked by an oxygen atom to form a phenoxazine ring.

Amine repeat units may be provided in a molar amount in the range of about 0.5 mol % up to about 50 mol %, optionally about 1-25 mol %, optionally about 1-10 mol %.

The polymer may contain one, two or more different repeat units of formula (IX).

Amine repeat units may provide hole-transporting and/or light-emitting functionality.

Polymer Synthesis

Preferred methods for preparation of polymers as described herein comprise a "metal insertion" wherein the metal atom of a metal complex catalyst is inserted between an aryl or heteroaryl group and a leaving group of a monomer (Im). Exemplary metal insertion methods are Suzuki polymerisation as described in, for example, WO 00/53656 and Yamamoto polymerisation as described in, for example, T. Yamamoto, "Electrically Conducting And Thermally Stable pi-Conjugated Poly(arylene)s Prepared by Organometallic Processes", Progress in Polymer Science 1993, 17, 1153-1205. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units illustrated throughout this application may be derived from a monomer carrying suitable leaving groups. Likewise, an end-capping group or side group carrying only one reactive leaving group may be bound to the polymer by reaction of a leaving group at the polymer chain end or side respectively.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular copolymers may be prepared when both reactive groups of a first monomer are boron and both reactive groups of a second monomer are halogen.

As alternatives to halides, other leaving groups capable of participating in metal insertion include sulfonic acids and sulfonic acid esters such as tosylate, mesylate and triflate.

Polymers as described herein suitably have a polystyrene-equivalent number-average molecular weight (Mn) measured by gel permeation chromatography in the range of about $1\times10^3$ to $1\times10^8$, and preferably $1\times10^3$ to $5\times10^6$. The polystyrene-equivalent weight-average molecular weight (Mw) of the polymers described herein may be $1\times10^3$ to $1\times10^8$, and preferably $1\times10^4$ to $1\times10^7$.

The polymers as described anywhere herein are suitably amorphous polymers.

Light-Emitting Layers

A light-emitting layer of an OLED may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display.

A polymer comprising a repeat unit of formula (I) may be provided as a light-emitting material in a light-emitting layer, or as a host for a fluorescent or phosphorescent dopant.

If a polymer comprising a repeat unit of formula (I) is used as a host material for a fluorescent or phosphorescent dopant then the lowest singlet excited state energy level or lowest triplet excited state energy level respectively of the polymer is preferably at least the same as, or no lower than, the corresponding energy level of the dopant.

Light emitted from a light-emitting layer, either from a polymer comprising a repeat unit of formula (I), a light-emitting dopant used in combination with a host polymer comprising a repeat unit of formula (I), or another light-emitting material, may be red, green or blue.

A blue emitting material may have a photoluminescent spectrum with a peak in the range of no more than 490 nm, optionally in the range of 420-480 nm.

A green emitting material may have a photoluminescent spectrum with a peak in the range of more than 490 nm up to 580 nm, optionally more than 490 nm up to 540 nm.

A red emitting material may optionally have a peak in its photoluminescent spectrum of more than 580 nm up to 630 nm, optionally 585-625 nm.

A light-emitting layer may contain a mixture of more than one light-emitting material, for example a mixture of light-emitting materials that together provide white light emission.

A white-emitting OLED may contain a single, white-emitting layer or may contain two or more layers that emit different colours which, in combination, produce white light.

White light may be produced from a combination of red, green and blue light-emitting materials provided in a single light-emitting layer distributed within two or more light-emitting layers.

The light emitted from a white-emitting OLED may have CIE x coordinate equivalent to that emitted by a black body at a temperature in the range of 2500-9000K and a CIE y coordinate within 0.05 or 0.025 of the CIE y co-ordinate of said light emitted by a black body, optionally a CIE x coordinate equivalent to that emitted by a black body at a temperature in the range of 2700-4500K.

Exemplary phosphorescent light-emitting materials include metal complexes comprising substituted or unsubstituted complexes of formula (X):

$$ML^1{}_qL^2{}_rL^3{}_s \qquad (X)$$

wherein M is a metal; each of $L^1$, $L^2$ and $L^3$ is a coordinating group; q is an integer; r and s are each independently 0 or an integer; and the sum of (a. q)+(b. r)+(c.s) is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet or higher states. Suitable heavy metals M include d-block metals, in particular those in rows 2 and 3 i.e. elements 39 to 48 and 72 to 80, in particular ruthenium, rhodium, palladium, rhenium, osmium, iridium, platinum and gold. Iridium is particularly preferred.

Exemplary ligands $L^1$, $L^2$ and $L^3$ include carbon or nitrogen donors such as porphyrin or bidentate ligands of formula (XI):

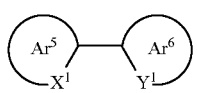

(XI)

wherein $Ar^5$ and $Ar^6$ may be the same or different and are independently selected from substituted or unsubstituted aryl or heteroaryl; $X^1$ and $Y^1$ may be the same or different and are independently selected from carbon or nitrogen; and $Ar^5$ and $Ar^6$ may be fused together. Ligands wherein $X^1$ is carbon and $Y^1$ is nitrogen are preferred, in particular ligands in which $Ar^5$ is a single ring or fused heteroaromatic of N and C atoms only, for example pyridyl or isoquinoline, and $Ar^6$ is a single ring or fused aromatic, for example phenyl or naphthyl.

Examples of bidentate ligands are illustrated below, each of which may be unsubstituted or substituted with one or more substituents:

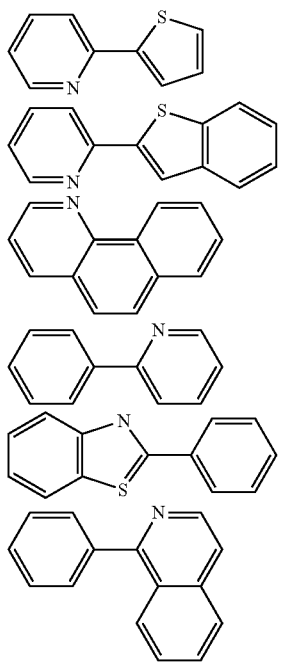

Each of $Ar^5$ and $Ar^6$ may carry one or more substituents. Two or more of these substituents may be linked to form a ring, for example an aromatic ring.

Other ligands suitable for use with d-block elements include diketonates, in particular acetylacetonate (acac); triarylphosphines and pyridine, each of which may be substituted.

Exemplary substituents include groups $R^{13}$ as described above with reference to Formula (IX). Particularly preferred substituents include fluorine or trifluoromethyl which may be used to blue-shift the emission of the complex, for example as disclosed in WO 02/45466, WO 02/44189, US 2002-117662 and US 2002-182441; alkyl or alkoxy groups, for example $C_{1-20}$ alkyl or alkoxy, which may be as disclosed in JP 2002-324679; carbazole which may be used to assist hole transport to the complex when used as an emissive material, for example as disclosed in WO 02/81448; and dendrons which may be used to obtain or enhance solution processability of the metal complex, for example as disclosed in WO 02/66552.

A light-emitting dendrimer typically comprises a light-emitting core bound to one or more dendrons, wherein each dendron comprises a branching point and two or more dendritic branches. Preferably, the dendron is at least partially conjugated, and at least one of the branching points and dendritic branches comprises an aryl or heteroaryl group, for example a phenyl group. In one arrangement, the branching point group and the branching groups are all phenyl, and each phenyl may independently be substituted with one or more substituents, for example alkyl or alkoxy.

A dendron may have optionally substituted formula (XII)

(XII)

wherein BP represents a branching point for attachment to a core and $G_1$ represents first generation branching groups.

The dendron may be a first, second, third or higher generation dendron. $G_1$ may be substituted with two or more second generation branching groups $G_2$, and so on, as in optionally substituted formula (XIIa):

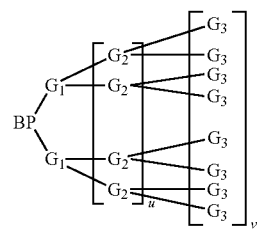

(XIIa)

wherein u is 0 or 1; v is 0 if u is 0 or may be 0 or 1 if u is 1; BP represents a branching point for attachment to a core and $G_1$, $G_2$ and $G_3$ represent first, second and third generation dendron branching groups. In one preferred embodiment, each of BP and $G_1$, $G_2$ . . . $G_n$ is phenyl, and each phenyl BP, $G_1$, $G_2$ . . . $G_{n-1}$ is a 3,5-linked phenyl.

A preferred dendron is a substituted or unsubstituted dendron of formula (XIIb):

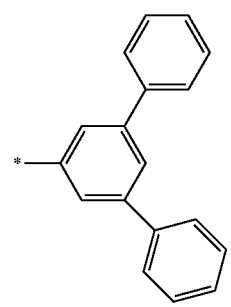

(XIIb)

wherein * represents an attachment point of the dendron to a core.

BP and/or any group G may be substituted with one or more substituents, for example one or more $C_{1-20}$ alkyl or alkoxy groups.

Phosphorescent light-emitting materials may be provided in a light-emitting layer with a host material. The host material may be a host polymer of the invention.

The phosphorescent light-emitting material may be physically mixed with a host material or may be covalently bound thereto. If the polymer comprising a repeat unit of formula (I) is used as a host material then the phosphorescent light-emitting material may be provided in a side-chain, main chain or end-group of the polymer. Where the phosphorescent material is provided in a polymer side-chain, the phosphorescent material may be directly bound to the backbone of the polymer or spaced apart there from by a spacer group, for example a $C_{1-20}$ alkyl spacer group in which one or more non-adjacent C atoms may be replaced by O or S. It will therefore be appreciated that a composition of the present invention may consist of or may comprise a polymer of the invention comprising repeat units of formula (I) with a phosphorescent light-emitting material bound to the polymer.

Charge Transporting and Charge Blocking Layers

A hole transporting layer may be provided between the anode and the light-emitting layer or layers of an OLED. Likewise, an electron transporting layer may be provided between the cathode and the light-emitting layer or layers.

Similarly, an electron blocking layer may be provided between the anode and the light-emitting layer and a hole blocking layer may be provided between the cathode and the light-emitting layer. Transporting and blocking layers may be used in combination. Depending on its HOMO and LUMO levels, a single layer may both transport one of holes and electrons and block the other of holes and electrons.

A charge-transporting layer or charge-blocking layer may be cross-linked, particularly if a layer overlying that charge-transporting or charge-blocking layer is deposited from a solution. The crosslinkable group used for this crosslinking may be a crosslinkable group comprising a reactive double bond such and a vinyl or acrylate group, or a benzocyclobutane group.

If present, a hole transporting layer located between the anode and the light-emitting layers preferably has a HOMO level of less than or equal to 5.5 eV, more preferably around 4.8-5.5 eV or 5.1-5.3 eV as measured by cyclic voltammetry. The HOMO level of the hole transport layer may be selected so as to be within 0.2 eV, optionally within 0.1 eV, of an adjacent layer (such as a light-emitting layer) in order to provide a small barrier to hole transport between these layers.

If present, an electron transporting layer located between the light-emitting layers and cathode preferably has a LUMO level of around 2.5-3.5 eV as measured by cyclic voltammetry. For example, a layer of a silicon monoxide or silicon dioxide or other thin dielectric layer having thickness in the range of 0.2-2 nm may be provided between the light-emitting layer nearest the cathode and the cathode. HOMO and LUMO levels may be measured using cyclic voltammetry.

A hole transporting layer may contain a polymer comprising a repeat unit of formula (I).

One or more of the repeat units of this polymer may be substituted with a crosslinkable group.

Exemplary hole-transporting polymers comprising a repeat unit of formula (I) include:

a copolymer comprising one or more repeat units of formula (I) wherein each m is 0, and one or more amine co-repeat units of formula (IX); and a homopolymer or copolymer comprising one or more repeat units of formula (I) wherein each m is 1.

Hole Injection Layers

A conductive hole injection layer, which may be formed from a conductive organic or inorganic material, may be provided between the anode 101 and the light-emitting layer 103 of an OLED as illustrated in FIG. 1 to assist hole injection from the anode into the layer or layers of semiconducting polymer. Examples of doped organic hole injection materials include optionally substituted, doped poly (ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. Nos. 5,723,873 and 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Cathode

The cathode 105 is selected from materials that have a workfunction allowing injection of electrons into the light-emitting layer of the OLED. Other factors influence the selection of the cathode such as the possibility of adverse interactions between the cathode and the light-emitting material. The cathode may consist of a single material such as a layer of aluminium. Alternatively, it may comprise a plurality of conductive materials such as metals, for example a bilayer of a low workfunction material and a high workfunction material such as calcium and aluminium, for example as disclosed in WO 98/10621. The cathode may comprise elemental barium, for example as disclosed in WO 98/57381, Appl. Phys. Lett. 2002, 81(4), 634 and WO 02/84759. The cathode may comprise a thin (e.g. 1-5 nm) layer of metal compound, in particular an oxide or fluoride of an alkali or alkali earth metal, between the organic layers of the device and one or more conductive cathode layers to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Formulation Processing

A formulation suitable for forming a charge-transporting or light-emitting layer may be formed from the composition or the polymer comprising repeat units of formula (I) dissolved in a solvent or solvent mixture. The composition may consist of the polymer comprising repeat units of formula (I) and the solvent(s), or it may contain further components such as light-emitting dopants.

Polymers comprising a repeat unit of formula (I) may show lower viscosity than their counterparts in which $R^2$ is absent. This may enable the preparation of relatively high concentration polymer formulations that are brought into the viscosity range suitable for the range of printing and coating techniques as described below, and provide for better control of the printing process. Control of polymer viscosity is particularly advantageous for inkjet printing of the polymer.

Solvents suitable for dissolving polymers comprising repeat units of formula (I), particularly polymers comprising alkyl substituents, include benzenes substituted with one or more $C_{1-10}$ alkyl or $C_{1-10}$ alkoxy groups, for example toluene, xylenes and methylanisoles.

Particularly preferred solution deposition techniques including printing and coating techniques such spin-coating and inkjet printing.

Spin-coating is particularly suitable for devices wherein patterning of the light-emitting layer is unnecessary—for example for lighting applications or simple monochrome segmented displays.

Inkjet printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, roll printing and screen printing.

EXAMPLES

Monomer Example 1

A monomer was prepared according to the following reaction scheme:

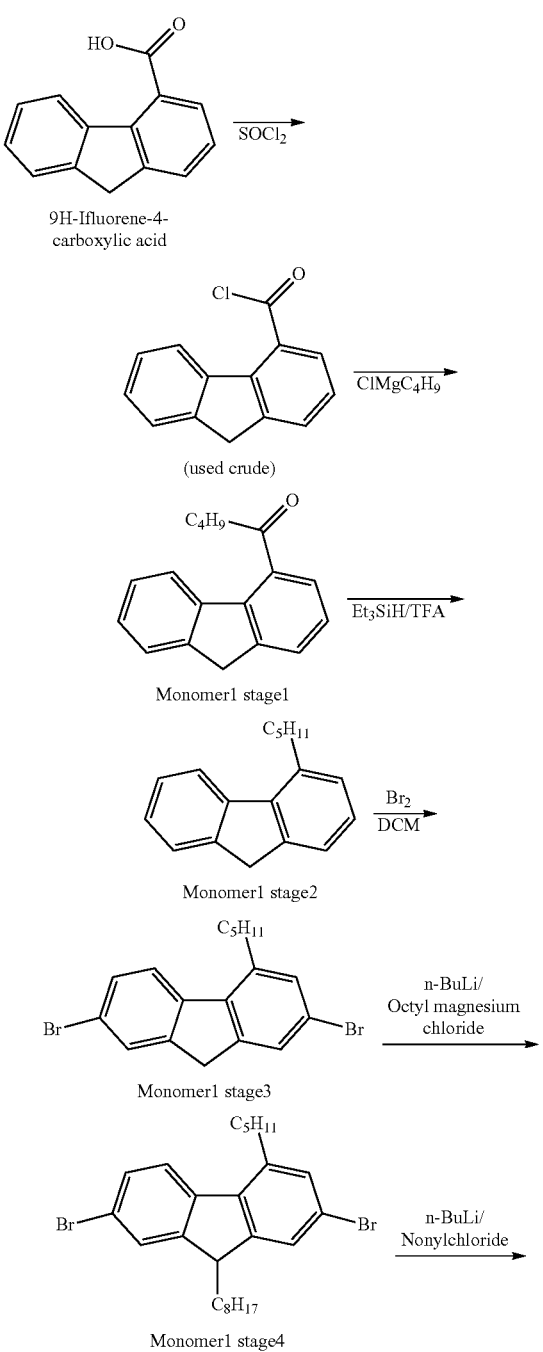

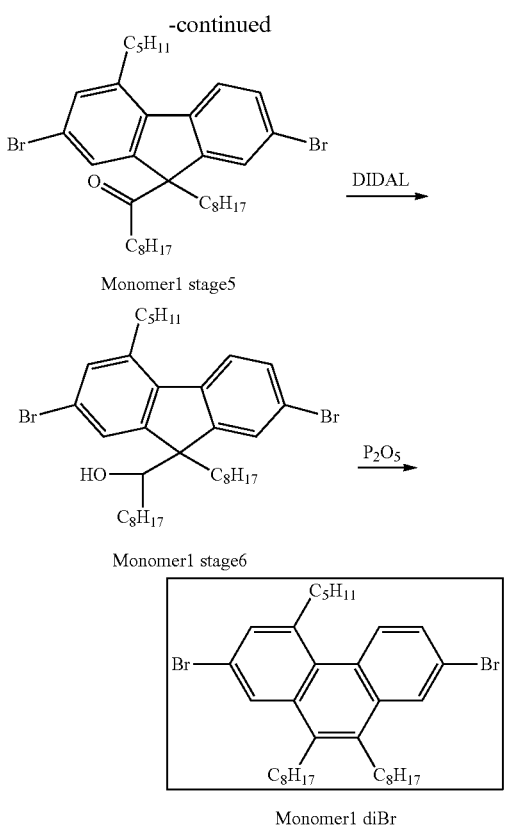

Monomer1 stage5

Monomer1 stage6

Monomer1 diBr

Synthesis of Monomer 1 Stage 1:

To a solution of 9H-fluorene-4-carboxylic acid (100 g, 0.47 mol) in 1 L toluene under inert gas (nitrogen) was added a catalytic amount of DMF followed by drop-wise addition of 70 mL (0.95 mmol) of thionyl chloride. The mixture was refluxed for 2.5 h under nitrogen and subsequently concentrated in vacuo to give a brown solid, which was fluorene-4-carboxylic acid chloride. The acid chloride was again dissolved in toluene and concentrated to a brown solid. To the solid 1 L of anhydrous tetrahydrofuran were added and the solution was cooled to −78° C. under nitrogen. To the stirred solution a THF solution of tert-butylmagnesium chloride (2M in THF, 235 mL, 0.47 mol) was added drop-wise in a rate so that the internal temperature does not exceed −75° C. The resulting mixture was allowed to warm up to room temperature overnight. GCMS showed conversion to mainly the desired product, Monomer stage1. The reaction was quenched with 100 mL of water, the organic layer was separated, the aqueous layer re-extracted with diethyl ether (100 mL), and the combined organic phases were concentrated to give a brown oil (120 g, 100% yield). The oil was identified as the desired Monomer stage1 by GCMS, and it was used in the following step without further purification.

Synthesis of Monomer 1 Stage 2:

To a solution of monomer stage 1 under nitrogen (120 g, 0.47 mol) in triethyl silane was added drop-wise trifluoroacetic acid (340 mL). During addition a gentle reflux of the reaction mixture was observed. After complete addition the resulting mixture was heated to 80° C. overnight. GCMS showed conversion to the product and a siloxane by-product. The mixture was concentrated in vacuo and the siloxane by-product was removed by distillation.

The now dark brown residue was dissolved in hexane (300 mL), washed twice with water (50 mL), dried over MgSO$_4$ and concentrated in vacuo to give an oil, which was Monomer stage2, 99% pure by GCMS (105 g, 94% yield). The oil was used in the subsequent step without any further purification.

Synthesis of Monomer 1 Stage 3:

Monomer stage2 (105 g, 0.45 mol) in 1 L dichloromethane (1.2 L) was cooled to 0° C. under nitrogen, and a solution of bromine (70 mL, 0.95 mol) in dichloromethane (200 mL) was added drop wise. After addition the solution was stirred at room temperature for 1 h. In process check by tlc showed full conversion. The mixture was quenched with 300 mL Na$_2$CO$_3$ solution (5% aq.). Phases were separated and the organic phase was washed with an aqueous solution of sodium thiosulphate. The organic layer was dried over MgSO$_4$ and concentrated to give a brown oil. The oil was vigorously stirred in acetonitrile until a yellow solid formed, which was filtered off. The solid was identified by NMR and GCMS as Monomer1 stage3 (154 g, 88% yield).

Synthesis of Monomer 1 Stage 4:

To a solution of Monomer 1 stage 3 (154 g, 0.39 mol) in diethyl ether under nitrogen was added drop-wise a solution of n-butyl lithium (2M in hexanes, 157 mL, 0.39 mol). After complete addition the reaction mixture was stirred for 2 h at room temperature. The mixture was then cannulated into a flask containing 1-bromooctane (90.8 g, 0.47 mol) under nitrogen. The receiver flask was cool to maintain the internal temperature below 30° C. The resulting mixture was left stirring overnight and subsequently quenched with HCl (2M, 200 mL). The phases were separated, the organic phase was washed with water, dried over MgSO$_4$, concentrated to give a yellow oil. The oil was triturated in acetonitrile to give a solid which was re-crystallised from a mixture of toluene and acteonitrile (1:1). The obtained yellow solid was Monomer1 stage4 (132 g, 67% yield).

Synthesis of Monomer 1 Stage 5:

Monomer1 stage4 (131 g, 0.258 mol) was dissolved under nitrogen in diethyl ether (2 L) and n-butyl lithium (2M in hexanes, 109 mL, 0.27 mol) was added drop-wise keeping the internal temperature below 30° C. Once the addition was completed, the dark red mixture was stirred at room temperature for 10 min and then cannulated into a flask containing nonylchloride (50.2 g, 0.28 mol). The resulting mixture was stirred for 1 h at room temperature after which full conversion was achieved monitored by GCMS. The reaction was quenched with water (500 mL), and stirred at room temperature for 20 min. The organic layer was separated, and the aqueous layer was extracted twice with diethyl ether. The combined organic phases were washed with a saturated solution sodium hydrogencarbonate, dried over MgSO$_4$. And concentrated to give a yellow oil, which was Monomer1 stage5 characterised by GCMS and $^1$H-NMR (160 g, 91% yield). This material was used in the next step without any further purification.

Synthesis of Monomer 1 Stage 6:

To a solution of Monomer1 stage5 (62 g, 95.9 mmol) in dichloromethane (1 L) under nitrogen was added a solution of diisobutylaluminium hydride (DIBAL) (1M in hexane, 144 mL, 0.143 mol) at 0° C. The resulting mixture was allowed to warm up to room temperature and stirred for another 2 h, after which process check showed full conversion to the desired Monomer1 stage6. The mixture was cooled to 0° C. and quenched with HCl aq. (1M, 200 mL). The aqueous layer was separated, the water phase re-extracted twice with dichloromethane, the combined organic phases were dried over MgSO$_4$, washed with concentrated aqueous solution of sodium hydrogencarbonate, and concentrated in vacuo to give an oil. The oil was purified by Silica column chromatography using a gradient of hexane:dichloromethane (0%→25% dichloromethane in hexane) to give 61 g (98% yield) Monomer1 stage6 as an oil, which solidifies while standing.

Synthesis of Monomer1 diBr:

To a solution of 58.8 g (90.7 mmol) Monomer1 stage6 in toluene under nitrogen (1.1 L) was added phosphorous pentoxide portion-wise (24.4 g, 0.172 mol). The resulting mixture was stirred at room temperature for 3 h, at which point the mixture had become dark green. In process check by tlc showed conversion to product. The mixture was cooled to 00 and 50 mL of water was added drop-wise. After 30 min stirring the slurry as concentrated in vacuo to remove the toluene and water (50 mL) and diethyl ether were added (100 mL). The mixture was stirred and the organic phase was separated. The aqueous phase was re-extracted twice with diethyl ether (100 mL).

The combined organic phases were washed with saturated solution of sodium hydrogen carbonate, dried over MgSO$_4$, and concentrated to give an oil. The oil was purified by repeated Silica column chromatography eluting with hexane, and the resulting oil was solidified by repeated vigorous stirring in methanol with the solvent decanted or filtered off between washes. 11.7 g were obtained at a purity of 98.4%, another 14.3 g were obtained in lower purity (45% overall yield).

Monomer Example 2

Monomer Example 2 was prepared according to the following reaction scheme:

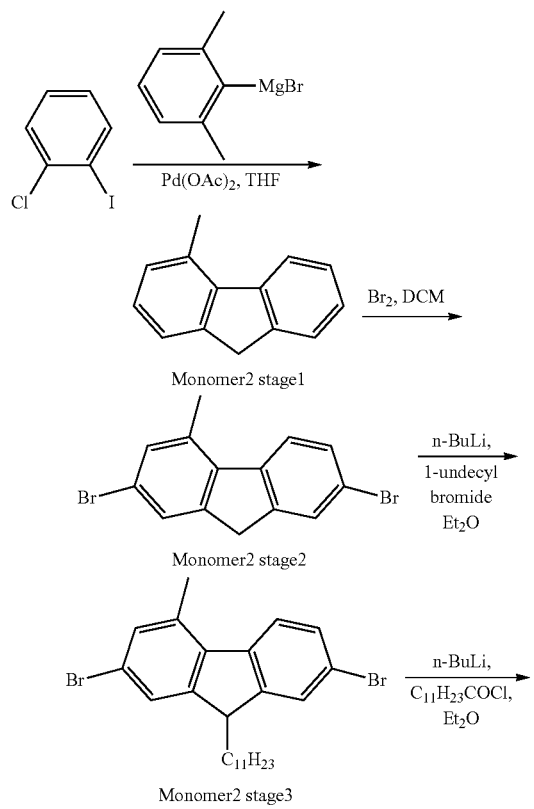

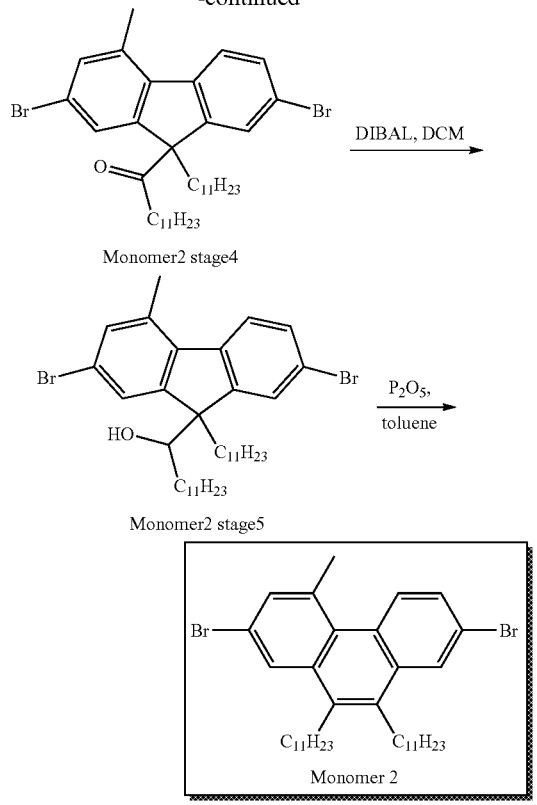

Synthesis of Monomer 2 Stage 1:

Under nitrogen, 1-chloro-2-iodobenzene (47.7 g, 0.2 mol) was dissolved in 550 mL anhydrous tetrahydrofuran. Palladium acetate (1.35 g, 6 mmol) was added and the mixture was heated to 60° C. 1,3-dimethylphenyl-2-magnesiumbromide (1M in THF, 400 mL, 0.4 mol) were added drop-wise in 3 portions. The internal temperature increases during addition to 68° C. After each portion conversion was checked to make sure the reaction was proceeding. Complete reaction after addition of all reagent was verified by $^1$H-NMR. The reaction mixture was cooled to room temperature and quenched with 100 mL HCl aq. (2M). The phases were separated, the aqueous phase was extracted with dichloromethane (3×100 mL), and the combined organic phases were dried over MgSO$_4$. Concentration in vacuo gave a brown oil, which was subjected to column chromatography to give 25.6 g (20% yield) of Monomer2 stage1 as a pale yellow oil which crystallises when standing.

Synthesis of Monomer 2 Stage 2:

Monomer 2 stage 1 (45 g, 0.25 mol) was dissolved in anhydrous dichloromethane and cooled to 0° C. under nitrogen. Bromine (71.8 g, 0.45 mol) in 92 mL dichloromethane were added drop-wise to the stirred solution. The reaction was left to warm overnight and in process check showed full consumption of starting material, but 5.4% of mono bromide present. Two additional portions of bromine (0.32 mL, 6.2 mmol) in 5 mL dichloromethane each were added to achieve 98.95% conversion to the desired dibromide, which is Monomer 2 stage 2. The reaction mixture was then quenched with saturated sodium hydrogencarbonate solution. Phases were separated, the aqueous phase was extracted twice with DCM (100 mL) and the combined organic phases were concentrated to dryness. Recrystallisation from toluene/methanol gave 57 g of Momomer2 stage2 as a white solid (HPLC purity 99.83%, 68% yield).

Synthesis of Monomer 2 Stage 3:

Monomer 2 stage 2 (57 g, 0.168 mol) were suspended in 2.5 L of diethyl ether under nitrogen. 68 mL (2M in hexane, 0.168 mol) of n-butyllithium (2M in hexanes) was added drop-wise. The reaction mixture turn dark red and almost all material dissolved. The mixture was cannulated into a flask containing 1-bomoundecane (59.5 mL, 0.252 mol) at 0° C. The reaction mixture was stirred for 3 days and quenched with HCl (2M, 200 mL). Phases were separated, the aqueous phase was re-extracted with diethyl ether (2×100 mL) and the combined organic phases were concentrated to give an orange oil. Stirring in acetonitrile (100 mL) overnight afforded a yellow solid which was filtered off, and dried in the oven. The solid was identified by GCMS and NMR as Monomer 2 stage 3 (49.7 g, 60% yield).

Synthesis of Monomer 2 Stage 4:

To Monomer 2 stage 3 (49 g, 0.1 mol) in 500 mL tetrahydrofuran was added potassium tert-butoxide (16.2 g, 0.144 mol) at 0° C. under nitrogen. A deep red solution formed, which was stirred for 1 h at room temperature. The mixture was cooled to 0° C. and a solution of 1-dodecanoyl-chloride (33 mL, 0.139 mol) in 100 mL THF was added drop-wise. The reaction was left to warm up while stirring overnight. The mixture was quenched at 0° C. with HCl (2M, 100 mL). The layers were separated, the aqueous phase was extracted twice with toluene (100 mL) and the combined organic phases were dried over MgSO₄ before concentrated in vacuo to afford a brown oil. The oil was diluted with hexane and filtered through a Silca plug eluting with hexane. Concentrating afforded a yellow oil, which was Monomer 2 stage 4 (62 g, 86% purity by HPLC). The product was used in the next step without any further purification.

Synthesis of Monomer 2 Stage 5:

Monomer 2 stage 4 (60 g, 0.089 mol) was dissolved in dichloromethane (900 mL) and cooled to 0° C. A solution of dibutylaluminium hydride in DCM (1M) was added drop-wise keeping the internal temperature at 0° C. The reaction mixture was stirred at room temperature for 2 h. The reaction mixture was cooled to 0° C. and quenched with HCl (2M, 200 mL). The layers were separated and the aqueous layer was extracted twice with DCM (200 mL). The combined organic layers were washed with a saturated solution of sodium hydrogecarbonate, dries over MgSO₄, and concentrated to afford an orange oil. The oil was diluted with hexane and filtered through a Silca plug eluting with hexane. Column chromatography afforded an oil which was Monomer 2 stage 5 (49 g, 81% yield).

Synthesis of Monomer 2 Dibromide:

Monomer 2 stage 5 (49 g, 0.072 mol) was dissolves in 900 mL toluene under nitrogen. Phosphorous pentoxide (19.5 g, 0.138 mol) was added portion wise to the mixture and the mixture was stirred for 1.5 h. The reaction was cooled with an ice bath and quenched by the addition of water (200 mL). Phases were separated, the aqueous phase was extracted with toluene (3×100 mL), the combined organic phases were dried over MgSO₄ and concentrated in vacuo to afford a yellow oil (46.9 g, 97% HPLC purity) which was Monomer2 dibromide, which contained an alkene impurity (3%). To remove the alkene impurity, repeated column chromatography and multi re-crystallisations from toluene/acetonitrile and ethyl actetate/ethanol were applied to afford Monomer 2 dibromide in high purity (13.04 g, 27% yield).

Polymer Examples

Polymers were prepared by Suzuki polymerisation of the following monomers according to the method described in WO 00/53656 in the amounts set out in Table 1. Molecular weights of polymers were controlled by using an imbalance (non 50:50 ratio) of boronic ester:halogen monomers.

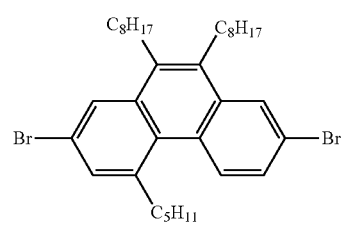

Monomer Example 1

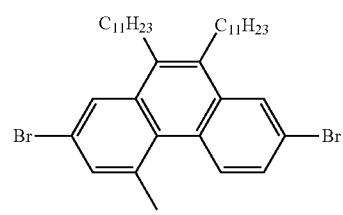

Monomer Example 2

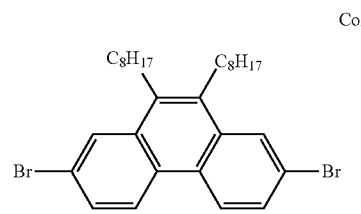

Comparative Monomer 1A

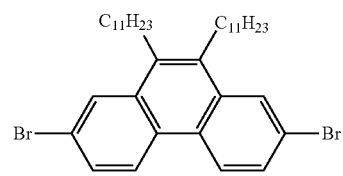

Compoerative Monomer 1B

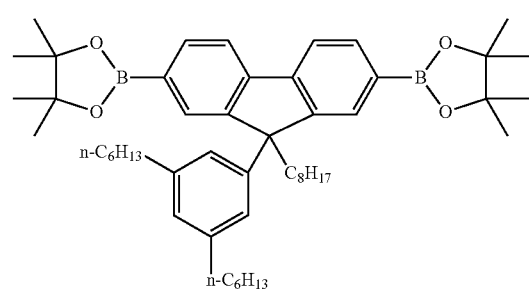

Monomer A

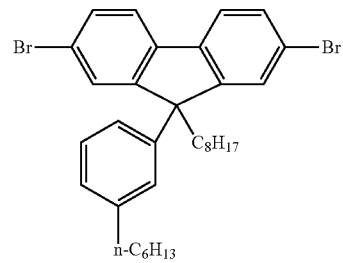

Monomer B

-continued

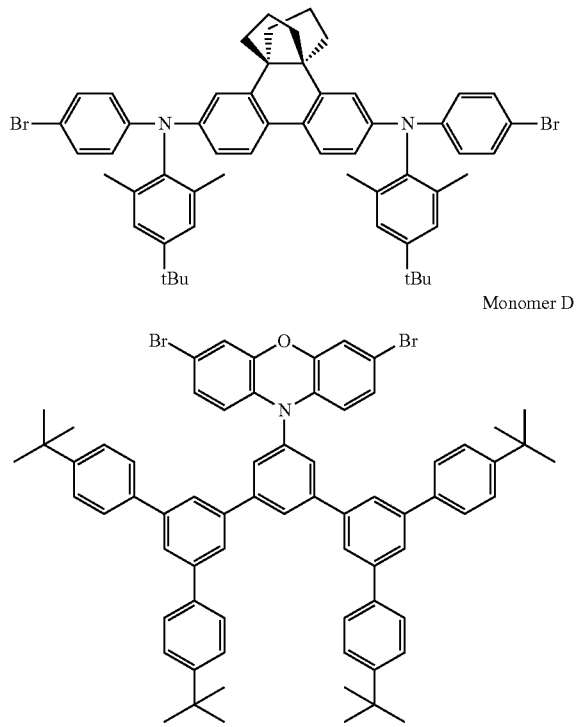

Monomer C (top structure)

Monomer D (bottom structure)

TABLE 1

| Polymer | Phenanthrene monomer (mol %) | A** (mol %) | B (mol %) | C (mol %) | D (mol %) | Mw × 10³ |
|---|---|---|---|---|---|---|
| Polymer Example 1 | Monomer Example 1 25 mol % | 50 | 19 | 4 | 2 | 258 |
| Comparative Polymer 1A | Comparative Monomer 1A 30 mol % | 50 | 14 | 5 | 1 | 266 |
| Comparative Polymer 1B* | Comparative Monomer 1B 25 mol % | 50 | 19 | 4 | 2 | 259 |
| Polymer Example 2 | Monomer Example 2 25 mol % | 50 | 19 | 4 | 2 | 244 |
| Comparative Polymer 2A* | Comparative Monomer 1B 25 mol % | 50 | 19 | 4 | 2 | 254 |

*Comparative Polymer 1B and Comparative Polymer 2A are formed using the same monomers, but the polymers are of different molecular weights.
**If needed for control of molecular weight, Monomer A was not used in an amount of exactly 50 mol %, e.g. in the range of 49-51 mol %, in order to provide a boronic ester: halogen monomer imbalance.

Formulation Examples 1 weight % solutions of Polymer Example 1, Comparative Polymer 1A and Comparative Polymer 1B were prepared by dissolving the polymers in a solvent mixture of 80% cyclohexylbenzene and 20% 4-methylanisole by volume. The viscosity of the resulting solutions is provided in Table 2.

Viscosity was measured at 20° C. with a cone (1°) and plate geometry using a controlled stress rheometer (TA instruments-AR1000).

TABLE 2

| Polymer | Viscosity (cP) |
|---|---|
| Polymer Example 1 | 13.9 |
| Comparative Polymer 1A | 70.1 |
| Comparative Polymer 1B | 17.3 |

The phenanthrene repeat unit of Polymer Example 1 and Comparative Polymer 1A have the same substituents $R^1$, but substituent $R^2$ is not present in Comparative Polymer 1A, resulting in a much higher viscosity of the formulation of Comparative Polymer 1A, despite similar molecular weights of the two polymers.

The viscosity of the formulation of Comparative Polymer 1B is significantly reduced as compared to Comparative Polymer 1A by providing larger substituents $R^1$ than Polymer Example 1 or Comparative Polymer 1A, but is still higher than viscosity of the formulation of Polymer Example 1.

1 weight % solutions of Polymer Example 2 and Comparative Polymer 2A were prepared by dissolving the polymers in a mixture of 80% cyclohexylbenzene and 20% 4-methylanisole by volume.

Figure 2:
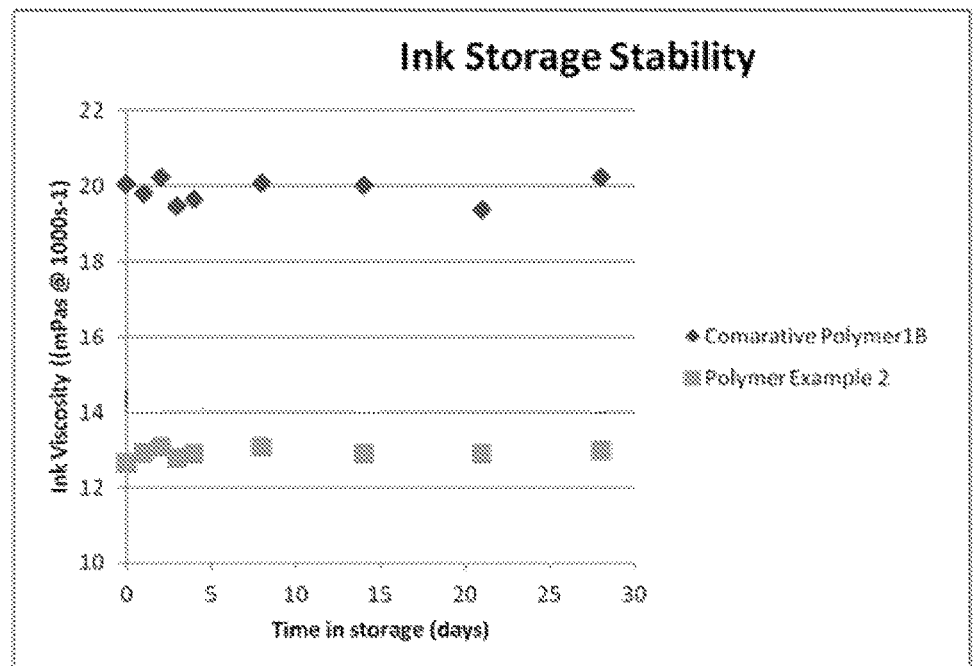
FIG. 2 is a graph of viscosity vs. time for a formulation according to an embodiment of the invention and comparative formulations.

With reference to FIG. 2, viscosity of the formulation of Polymer Example 2 is stable over time. The viscosity of the formulation of Polymer Example 2 is significantly lower than that of Polymer Example 2A, which has the same substituents $R^1$ as Polymer Example 2 but no substituent $R^2$.

Device Example 1

A blue organic light-emitting device having the following structure was prepared:

ITO/HIL/HTL/LE/Cathode wherein ITO is an indium-tin oxide anode; HIL is a hole-injecting layer; HTL is a hole-transporting layer; LE is a light-emitting layer; and the cathode comprises a layer of sodium fluoride in contact with the light-emitting layer and a layer of silver and a layer of aluminium.

To form the device, a substrate carrying ITO was cleaned using UV/Ozone. The hole injection layer was formed by spin-coating an aqueous formulation of a hole-injection material available from Plextronics, Inc. and heating the resultant layer. The hole transporting layer was formed by spin-coating a polymer comprising phenylene repeat units of formula (VIa), amine repeat units of formula (IX-1) and crosslinkable repeat units of formula (VIIa) and crosslinking the polymer by heating. The light-emitting layer was formed by spin-coating composition of Polymer Example 2 and an additive polymer. The cathode was formed by evaporation of a first layer of sodium fluoride to a thickness of about 2 nm, a second layer of aluminium to a thickness of about 100 nm and a third layer of silver to a thickness of about 100 nm.

Comparative Device 1

Figure 3:
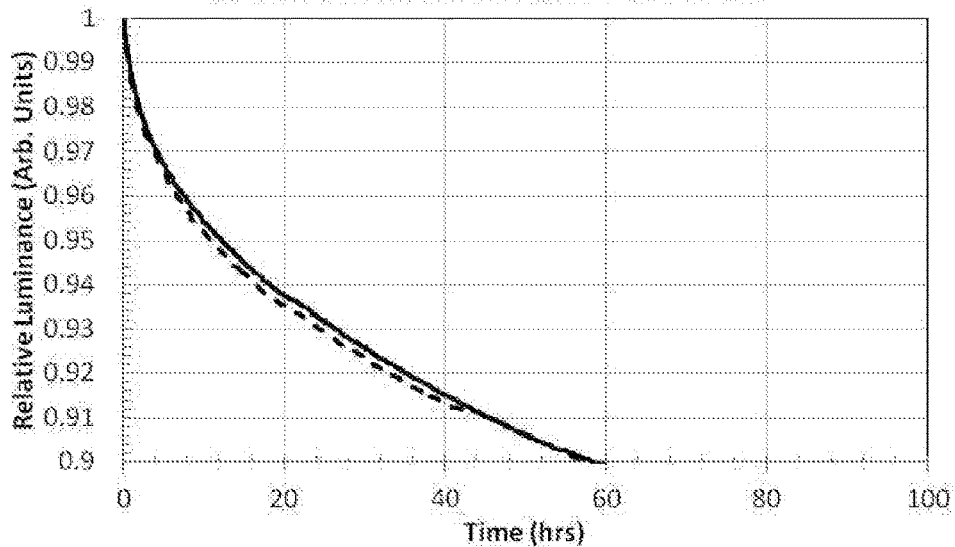
FIG. 3 is a graph of luminance vs. time for a device according to an embodiment of the invention and a comparative device.
Figure 4:
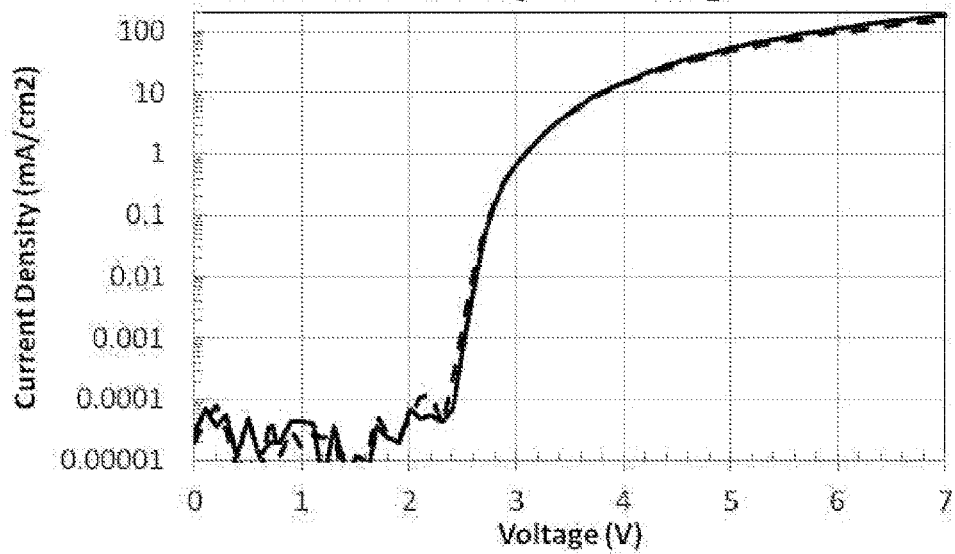
FIG. 4 is a graph of current density vs. voltage for a device according to an embodiment of the invention and a comparative device.
Figure 5:
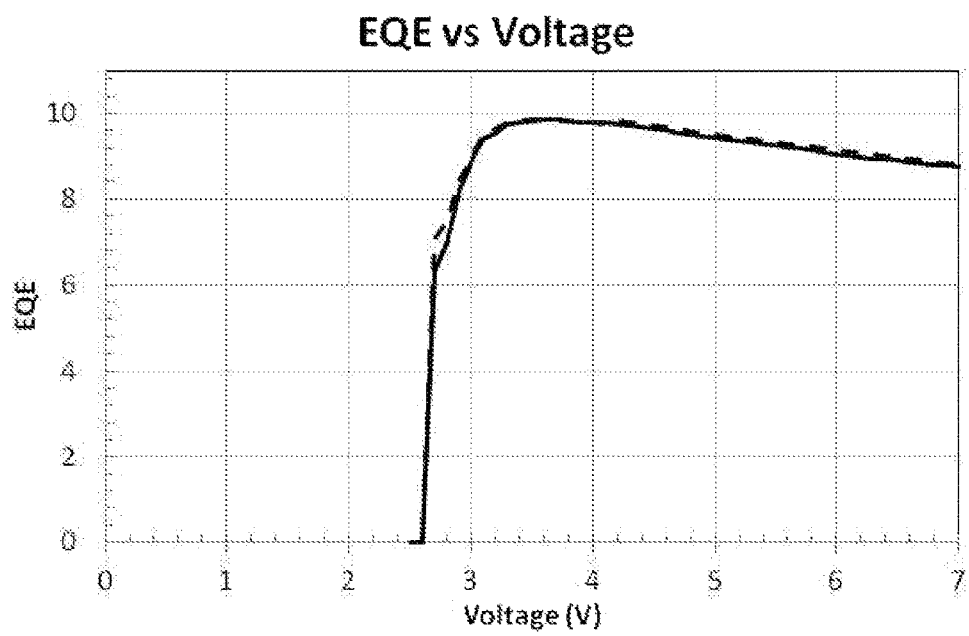
FIG. 5 is a graph of external quantum efficiency (EQE) vs. voltage for a device according to an embodiment of the invention and a comparative device.

A device was prepared as described for Device Example 1 except that Polymer Example 2 was replaced with Comparative Polymer 1B. As shown in FIGS. 3-5, device performance of Device Example 1 and Comparative Device 1 are similar.

With reference to FIG. 3 time taken for brightness to fall to 90% of an initial value is very similar for Device Example 1 (solid line) and Comparative Device 1 (dotted line).

With reference to FIG. 4, current density at a given voltage is very similar for Device Example 1 (solid line) and Comparative Device 1 (dotted line).

With reference to FIG. 5, external quantum efficiency at a given voltage is very similar for Device Example 1 (solid line) and Comparative Device 1 (dotted line).

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A conjugated polymer comprising a repeat unit of formula (III):

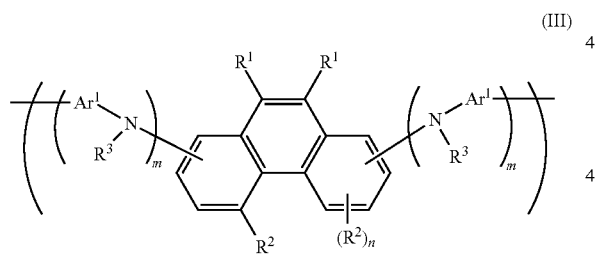

(III)

wherein:
$R^1$ in each occurrence is independently H or a substituent, and the two groups $R^4$ are optionally linked to form a ring;
$R^2$ in each occurrence is independently a substituent selected from a $C_{1-20}$ alkyl group, wherein one or more non-adjacent C atoms are optionally replaced with O, S, $NR^4$, C=O, or —COO—, $R^4$ is a substituent, and wherein one or more H atoms of the $C_{1-20}$ alkyl group are optionally replaced with F; and an aryl or heteroaryl group that is substituted or unsubstituted with one or more substituents;
$Ar^1$ in each occurrence is independently an aryl or heteroaryl group that is unsubstituted or substituted with one or more substituents;
$R^3$ in each occurrence is independently a substituent;
n is 0, 1, 2 or 3; and
each m is independently 0 or 1.

2. The polymer according to claim 1, wherein the repeat unit of formula (III) has formula:

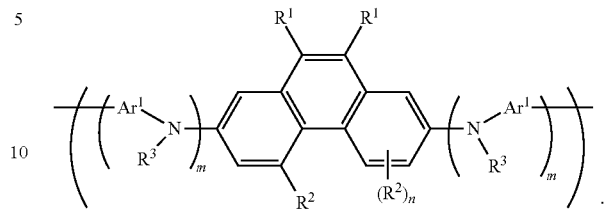

3. The polymer according to claim 1, wherein each $R^1$ is independently selected from the group consisting of a $C_{1-30}$ alkyl group, wherein one or more non-adjacent C atoms are optionally replaced with O, S, $NR^4$, C=O, or —COO—, wherein $R^4$ is a substituent, and wherein one or more H atoms of the $C_{1-30}$ alkyl group are optionally replaced with F; and an aryl or heteroaryl group that is substituted or unsubstituted with one or more substituents.

4. The polymer according to claim 1, wherein each $R^2$ is independently a $C_{1-10}$ alkyl group.

5. The polymer according to claim 1, wherein n is 0.

6. The polymer according to claim 1, wherein each m is 0.

7. The polymer according to claim 1, wherein at least one m is 1.

8. The polymer according to claim 7, wherein $Ar^1$ in each occurrence is independently a phenyl group that is unsubstituted or substituted with one or more substituents.

9. The polymer according to claim 7, wherein $R^3$ in each occurrence is independently a $C_{1-40}$ hydrocarbyl group.

10. The polymer according to claim 1, wherein the polymer comprises 1-50 mol % of the repeat unit of formula (I).

11. A monomer of formula (IIIm):

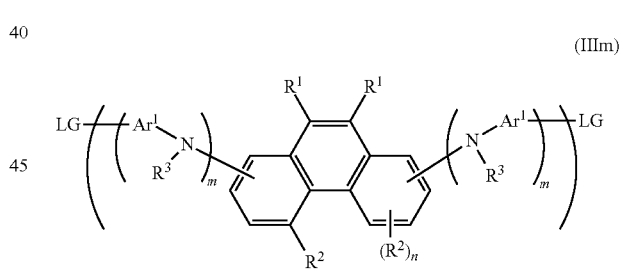

(IIIm)

wherein:
$R^1$ in each occurrence is independently H or a substituent;
$R^2$ in each occurrence is independently a substituent selected from a $C_{1-20}$ alkyl group, wherein one or more non-adjacent C atoms are optionally replaced with O, S, $NR^4$, C=O, or —COO—, $R^4$ is a substituent, and wherein one or more H atoms of the $C_{1-20}$ alkyl group are optionally replaced with F; and an aryl or heteroaryl group that is substituted or unsubstituted with one or more substituents;
$Ar^1$ in each occurrence is independently an aryl or heteroaryl group that is unsubstituted or substituted with one or more substituents;
$R^3$ in each occurrence is independently a substituent;
n is 0, 1, 2 or 3;
each m is independently 0 or 1; and
LG is a leaving group.

12. The monomer according to claim 11, wherein each LG is independently selected from boronic acid, boronic acid ester, halogen, and sulfonic acid ester.

13. A method of forming a polymer comprising the step of polymerizing a monomer according to claim 11.

14. The method according to claim 13, wherein the polymerizing step is performed in the presence of a metal catalyst.

15. A formulation comprising a polymer according to claim 1 and one or more solvents.

16. An organic electronic device comprising a first layer comprising a polymer according to claim 1.

17. The organic electronic device according to claim 16, wherein the device is an organic light-emitting device comprising an anode, a cathode, and at least one organic semiconducting layer including an organic light-emitting layer between the anode and the cathode, wherein the at least one organic semiconducting layer comprises the first layer.

18. A method of forming an organic light-emitting device comprising an anode, a cathode, and an organic semiconducting layer, the method comprising the steps of:
   depositing the formulation according to claim 15 over one of the anode and cathode;
   evaporating the one or more solvents to form the organic semiconducting layer comprising the polymer; and
forming the other of the anode and cathode over the organic semiconducting layer.

19. The method according to claim 18, wherein the formulation is deposited by inkjet printing.

20. The polymer according to claim 6, wherein the repeat unit of formula (III) is bound directly to aromatic carbon atoms of adjacent repeat units.

* * * * *